United States Patent [19]
Schwab et al.

[11] Patent Number: 5,749,852
[45] Date of Patent: May 12, 1998

[54] SHEATH SYSTEM FOR AUTOPERFUSION DILATATION CATHETER BALLOON

[75] Inventors: Sharon Schwab, San Diego; Glen L. Lieber, Poway; Don H. Tran, Westminster; Michael P. Brose; Maritess E. Minas, both of San Diego, all of Calif.

[73] Assignee: Medtronic, Inc., Minneapolis, Minn.

[21] Appl. No.: 685,119

[22] Filed: Jul. 23, 1996

[51] Int. Cl.⁶ .................................................. A61M 29/00
[52] U.S. Cl. ........................................... 604/96; 606/194
[58] Field of Search ............................. 604/96–103, 264, 604/280; 606/192, 194

[56] References Cited

U.S. PATENT DOCUMENTS

| | | | |
|---|---|---|---|
| 3,438,375 | 4/1969 | Ericson | 128/349 |
| 4,195,637 | 4/1980 | Grüntzig et al. | 128/348 |
| 4,637,396 | 1/1987 | Cook | 128/344 |
| 4,706,670 | 11/1987 | Andersen et al. | 128/344 |
| 4,762,130 | 8/1988 | Fogarty et al. | 128/348 |
| 5,181,911 | 1/1993 | Shturman | 604/96 |
| 5,295,959 | 3/1994 | Gurbel et al. | 604/96 |
| 5,308,356 | 5/1994 | Blackshear, Jr. et al. | 606/194 |
| 5,484,411 | 1/1996 | Inderbitzen et al. | 604/96 |
| 5,554,119 | 9/1996 | Harrison et al. | 604/96 |
| 5,556,382 | 9/1996 | Adams | 604/96 |

*Primary Examiner*—Corrine M. McDermott
*Attorney, Agent, or Firm*—John R. Duncan; Dianne M. F. Plunkett; Harold R. Patton

[57] ABSTRACT

A sheath arrangement for spiral balloon catheters which permits improved perfusion during dilation of a body vessel. Methods of making the sheath and assembling the sheath onto a balloon and the resulting sheathed balloon catheter are included. A tube sized to fit over a spiral balloon is cut, preferably by laser cutting, to form ribs extending from the tube ends with collars at the distal ends of the ribs. Preferably, the tube ends are trimmed to match the balloon spiral lobes. The sheath is placed over the spiral balloon, bonded to the balloon lobes. The collars are secured to the catheter adjacent to the balloon. When the balloon is expanded to dilate a body vessel, blood can freely pass through the interlobe channels while the sheath prevents entry of arterial intima from entering into the channels. The rib and collar arrangement securely maintains the sheath in place on the balloon.

16 Claims, 5 Drawing Sheets

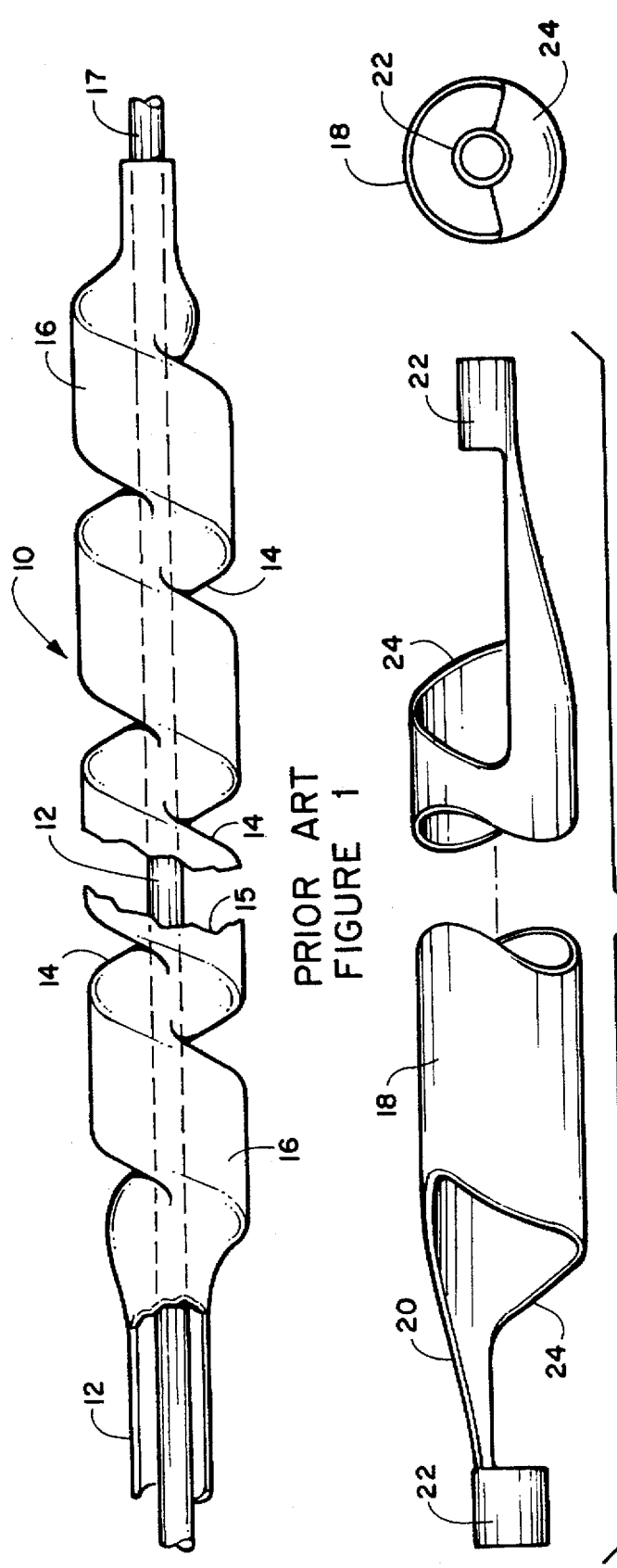

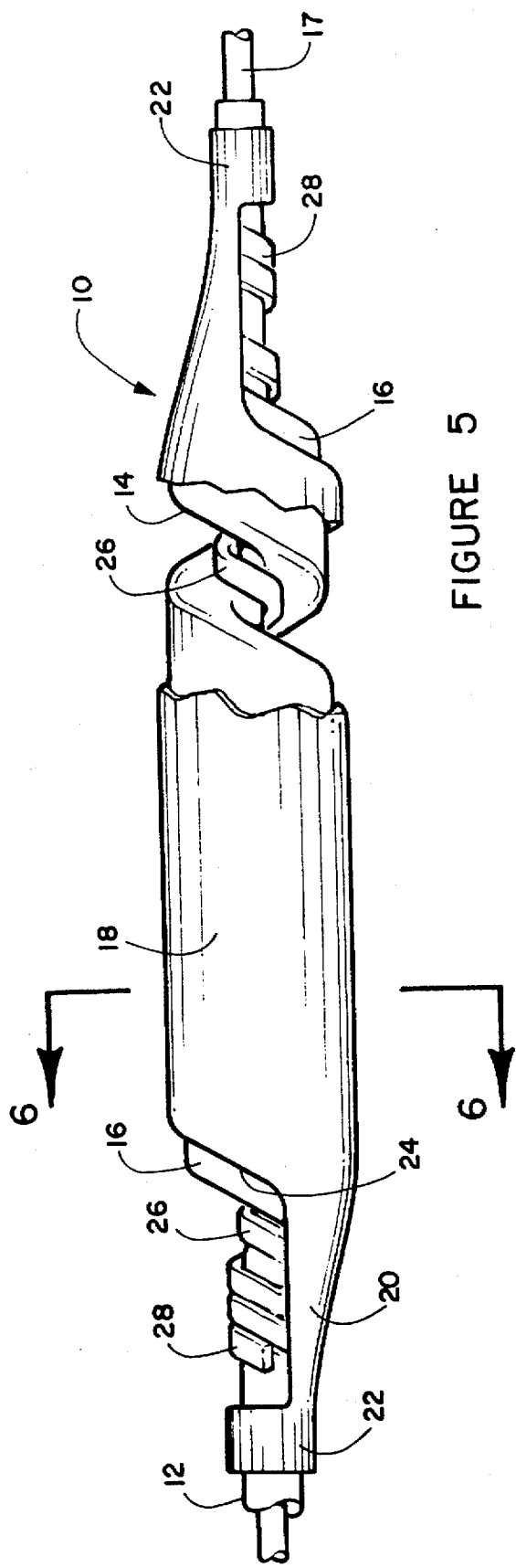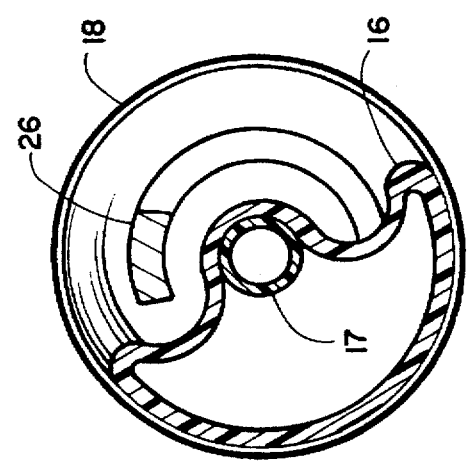
FIGURE 5
FIGURE 6

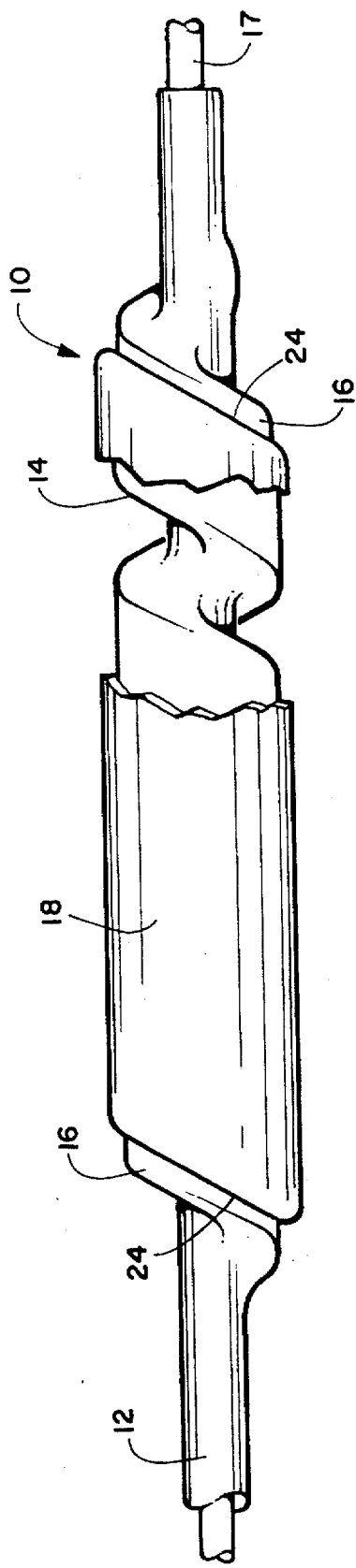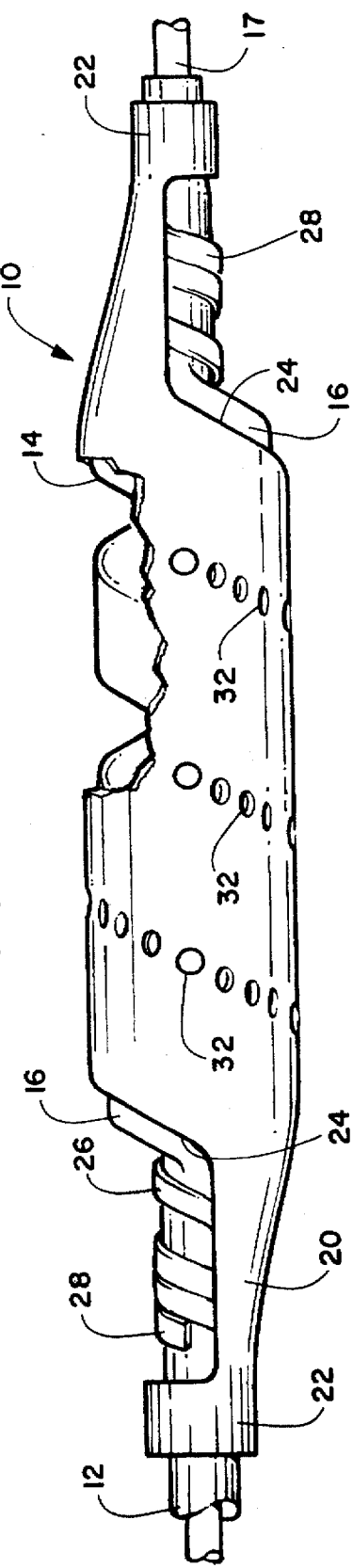

SHEATH SYSTEM FOR AUTOPERFUSION DILATATION CATHETER BALLOON

BACKGROUND OF THE INVENTION

This invention relates to methods and apparatus for improving the performance of autoperfusion dilatation catheters as used in angioplasty and the like.

Dilatation balloon catheters are well known and used regularly for coronary angioplasty procedures and other similar procedures. Atheromatous plaque adhering to a blood vessel wall and restricting blood flow therethrough is compressed against the vessel wall by a balloon that is positioned in the vessel at the plaque location. This dilates the vessel lumen to permit increased blood flow.

A typical balloon catheter includes two lengthwise lumens or channels, one for inflation of an inflatable balloon sealed to the distal catheter end and the other for insertion of a guidewire extending through the catheter to aid in positioning the catheter during use.

Many catheters have been designed for particular uses, having a variety of configurations, methods of construction and methods of use. Most have a generally tubular balloon that, when inflated, temporarily cuts off blood flow through the vessel. Serious consequences can occur when blood flow is stopped for an extended period. Therefore, inflation duration is generally relatively short, typically no more than 150–180 seconds. Longer inflation periods would be very desirable, since better plaque compression could be accomplished. Also, some patients cannot tolerate even short time blood occlusion in some vessels.

Attempts have been made to develop balloon configurations that will permit at least some continued blood flow during plaque compression. For example, catheters having an additional lumen have been used, with openings between the catheter exterior and the added lumen at both ends of the balloon, so that limited blood flow can bypass the balloon occlusion. However, this arrangement has had limited success, since only a very limited amount of blood can flow though the lumen and adding the lumen increases the diameter of the catheter, which itself will tend to retard blood flow. Thus, at most this arrangement will allow a very slightly longer balloon inflation period.

Blackshear et al. in U.S. Pat. No. 5,308,356 and others have disclosed catheter balloons with a spiral or corkscrew-like configuration when expanded. Such perfusion balloon catheters are intended to allow blood to flow in a spiral channel path past the balloon during balloon inflation. However, in practice, little if any blood flow is found to occur with these spiral balloons, apparently due to blockage of the balloon channels by the arterial intima or lining. Other spiral balloons have been used for other purposes, such as the Fogarty et al. arrangement described in U.S. Pat. No. 4,762,130 for embolectomy.

In attempting to overcome these channel blockage problems, generally tubular sheaths have been provided over the spiral balloon, as disclosed by Gurbel et al. in U.S. Pat. No. 5,295,959 and by Cordis in U.S. Pat. No. 5,484,411. These sheaths cover the outer portions of the balloon spiral lobe and resist entry of arterial intima into the spiral channels when the balloon is inflated. While often effective in increasing blood flow past the balloon, these sheaths are typically unbonded or only bonded by heat or adhesive to narrow lines along the balloon spiral and may come loose in use in a blood vessel, to the serious detriment of the patient. Further, "tenting" also occurs in the middle channels of a spiral balloon, with the sheath tending to fold into the channel, where the sheath is not bonded to the spiral under tension.

Such sheaths are also difficult to manufacture in a manner that will resist tearing of sheath end edges when in use and when being moved along a vessel to the desired location. Ends of the sheath that are located at narrower balloon end regions may result in the sheath ends folding or "tenting" into the spiral channels, decreasing blood flow. Any tears at the sheath ends will aggravate this channel blocking tendency.

Therefore, there is a continuing need for improvements in autoperfusion dilatation catheters to increase blood flow past an inflated balloon while maintaining the desired dilatation effect with respect to plaque or the like, to improve resistance to channel blockage of all channels, especially at sheath ends, to reduce sheath end tearing and resulting channel restrictions, and to improve securing of a sheath to a catheter and balloon to prevent disengagement of the sheath from the balloon.

SUMMARY OF THE INVENTION

The above-noted problems, and others, are overcome in accordance with this invention by a sheath for a spiral balloon catheter and an assembly of spiral balloon and surrounding sheath that basically comprises a generally tubular body having a diameter selected to fit snugly over a spiral balloon, having ends configured to match the end spiral lobes and secured to the spiral balloon. In one preferred embodiment, a rib extends from at least one end of the tubular body and a collar at the distal end of the rib is secured to the catheter.

Where the spiral balloon is formed from a compliant material, such as polyethylene, that will expand when subjected to high internal fluid pressure, a retaining wire which follows the balloon channels and is secured to the catheter beyond the balloon edges is preferred. Where the spiral balloon is formed from a non-compliant material such as polyethylene terephthalate which will not appreciably expand or stretch when subjected to high internal fluid pressure, the retaining wire is preferably omitted to provide a lower wrapped profile. Omitting the retaining wire results in lower production costs, simplifies assembly and increases tracking flexibility.

The assembly of sheath and catheter balloon is basically prepared by sliding the sheath over the balloon, bonding the sheath to the spiral balloon lobes and bonding the collars to the catheter adjacent to the balloon. Generally, the collars are preformed into tubular shapes. The collar at one end is slipped over the catheter as the sheath is slipped over the balloon, with the collar at the opposite sheath end being split longitudinally so as to be expanded at the slit, placed over the catheter and bonded in place.

The sheath, ribs and collars are preferably cut from a single tubular preform by laser cutting. We have found laser cutting to be precise, rapid and to form a very small, uniform bead along the cut edges which is surprisingly resistant to tearing when compared to mechanically (e.g., knife) cut edges.

The rib is a narrow strip of sheath material extending axially away from the sheath end. Preferably, the sheath end edge is cut in a spiral pattern conforming to the balloon lobe shape, from one edge of the rib around to an axial line corresponding to the other rib edge. The sheath is bonded to the balloon by any suitable method, such as adhesive bonding, heat bonding, laser bonding, etc. For heat or laser bonding, a heat activated surface layer may be used or direct bonding of the sheath and balloon materials may be accomplished.

The sheath is preferably bonded to the balloon with a suitable adhesive using any suitable application technique. Typically, a continuous bond may be formed by inserting a small needle dispenser between sheath and the pressurized balloon (typically at 10–40 psig), infusing an appropriate amount of adhesive and allowing the adhesive to wick along the balloon lobes. Alternatively, the adhesive may be applied as a discontinuous band circumferentially across the balloon lobes or at selected points along the lobes. By omitting adhesive in areas where the balloon is folded, stresses on the adhesive layer are minimized.

Any suitable adhesive may be used. Typically, a self-curing liquid adhesive such as a cyanoacrylate, a UV cured adhesive, such as the Loctite® 33xx series or a polyurethane epoxy such as the H. B. Fuller UR-0531 A/B may be used. Alternately, a heat or radiation activated dry adhesive could be used and activated to form a bond after assembly of the sheath and balloon. In some cases, multiple adhesives may be preferred, e.g., a flexible UV cured adhesive to bond the major balloon lobes where flexibility and moderate bond strength is desired and a cyanoacrylate to bond the end lobes and collars where high bond strength is needed.

Where the balloon is non-compliant, the end rib and collar assemblies can be omitted, since the adhesive bonding of the sheath to the balloon will hold the sheath in place. In this embodiment, it is important that the ends of the sheath be configured to match the spiral balloon ends, with the sheath edge lying entirely along the end lobe and well bonded thereto.

While the sheath arrangement and assembly of this invention may be used with any suitable balloon configuration, optimum results are obtained with a spiral configuration in which the lobes have flattened-appearing peaks lying along a cylindrical surface, with the channels between lobes being narrow and deep. Wide lobes provide more effective dilatation while wider channels provide improved perfusion.

Where the balloon is formed from a compliant material, a retaining wire following the spiral channels and wrapped around the catheter adjacent to the balloon is preferred. In the case of a non-compliant balloon, the retaining wire may generally be omitted.

In some cases, the desired site for use of a balloon catheter in a main blood vessel may have a side vessel coming off the main vessel at that site. Perfusion of blood through both the main vessel and the side vessel during balloon expansion is highly desirable. In order to provide such side vessel perfusion, openings are preferably provided through the wall of the sheath aligned with the spiral balloon channels. These side perfusion opening may have any suitable size, pattern and shape.

BRIEF DESCRIPTION OF THE DRAWINGS

Details of the invention, and of preferred embodiments thereof, will be further understood upon reference to the drawing, wherein:

FIG. 1 is a side elevation view of a spiral balloon portion of a balloon catheter of the prior art;

FIG. 2 is a side elevation view of balloon sheath of this invention with rib and collar at each end;

FIG. 3 is an end elevation view of the balloon sheath of FIG. 2;

FIG. 4 is a plan view of the balloon sheath of FIG. 2;

FIG. 5 is a side elevation view of the balloon sheath in place on a spiral balloon having a retaining wire;

FIG. 6 is a section view taken on line 6—6 in FIG. 5;

FIG. 9 is a side elevation view of a balloon sheath without end ribs and collars;

FIG. 12 is an elevation view of a balloon sheath having side perfusion openings.

DETAILED DESCRIPTION OF PREFERRED EMBODIMENTS

Figure 7:
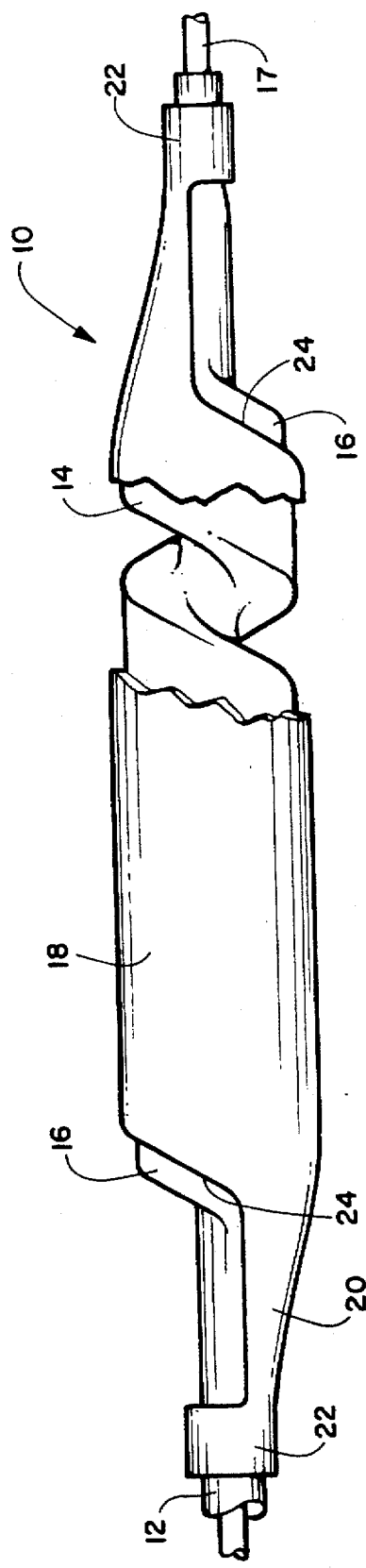
FIG. 7 is side elevation view of a balloon sheath in place on a spiral balloon without a retaining wire.

Referring to FIG. 1, there is seen a side view of a prior art spiral balloon of the sort intended for dilatation of lesions in body lumens while allowing continued blood flow past the dilatation. Low blood flow occurs with this spiral configuration, as with other spiral configurations, apparently due to blockage of the spiral channels by the arterial intima.

A balloon 10 is secured to an elongated catheter 12 in a conventional manner, as seen at the short cut away section at the left end in FIG. 1, so as to receive a gas or other fluid though a lumen extending through catheter 12. Catheter 12 extends through the balloon (as seen at the cut away center section 15) to distal end 17. When inserted into a body vessel, such as an artery, balloon 10 is wrapped so as to present a small balloon crossing profile. When the balloon has been positioned adjacent to a lesion, a fluid is introduced into balloon 10 which expands to dilate the lesion. Perfusion past balloon 10 is permitted by channels 14 between lobes 16. The greater the blood flow, the longer the balloon may be maintained in the expanded state and the greater the effectiveness of the dilatation in the opinion of many cardiologists. However, arterial intima tends to partially fill, or even block perfusion, severely limiting the length of time dilatation can be continued.

Sheath 18, as seen in FIGS. 2–4, when properly emplaced over balloon 10 greatly improves perfusion and allows much longer dilatation periods. The complete assembly of balloon and sheath is shown in FIG. 5.

Sheath 18 basically comprises a thin walled plastic tube having a diameter sized to fit over an expanded catheter balloon. Preferably, the inside diameter of sheath 18 is from about 97 to 99 percent of the outside diameter of expanded balloon 10, so that the sheath is stretched tightly between lobes 16 across channels 14 when the balloon is expanded to prevent "tenting" of the sheath into the balloon channels.

Any suitable material may be used for sheath 18. Preferably, the material is flexible, non-compliant or semi-compliant and high pressure resistant. Typical materials include polyamide (e.g., nylon 6 or 12), polyethylene, polyvinyl chloride, polyethylene terephthalate, ethylene-vinyl acetate copolymer, polyurethane and mixtures and combinations thereof. Excellent results are achieved with Nylon, such as Nylon 12 from Vestamid. Depending upon the adhesive selected to bond sheath 18 to balloon 10, the bonding surfaces may benefit from a pretreatment, such as by plasma etch, corona discharge, etc.

Figure 8:
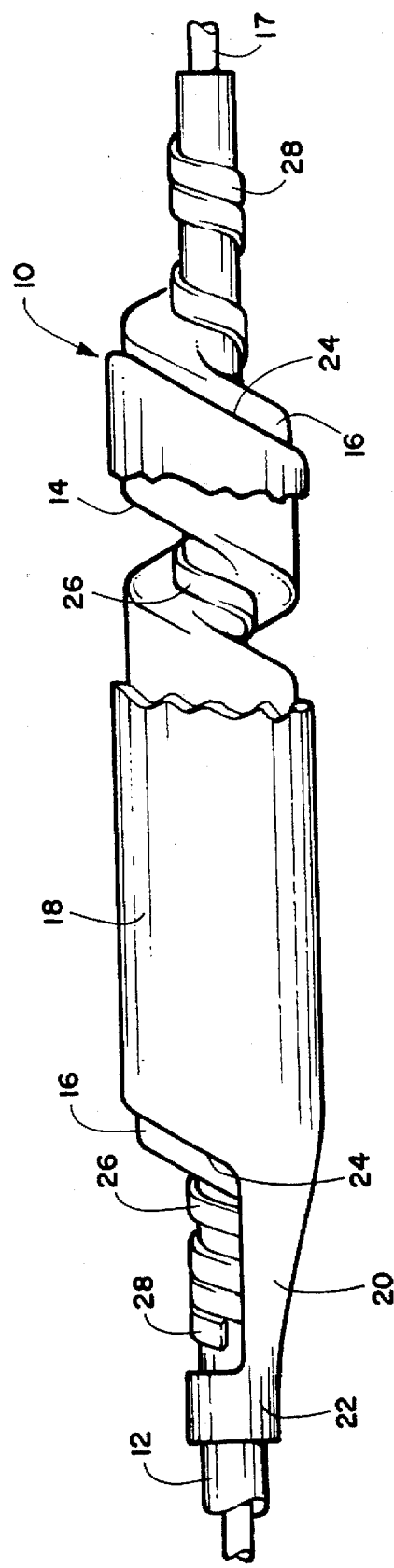
FIG. 8 is a side elevation view of a balloon sheath having a single end rib and collar in place on a spiral balloon with retaining wire.

In some cases, particularly where the spiral balloon is formed from a compliant material, one or both ends of sheath 18 include a rib 20 extending axially from the sheath tube, as seen in FIGS. 8 and 5, respectively. Preferably, each rib has a width about 40 to 60 per cent of the diameter of the sheath, so as to provide the necessary strength without obstructing perfusion.

A collar 22 is formed at the distal end of each rib 20 for securing sheath 18 to catheter 12. As seen in FIG. 4, collar 22 is cut from the tube material, preferably from the neck end of the sheath to form a sheet 23 shown in broken lines that is rolled to form a collar shape conforming to the outside shape of catheter 12. The rolled collar 22 surfaces are bonded with a suitable adhesive. For ease of assembly where a rib and collar combination is used at each end of balloon 18 as shown in FIGS. 2–5, one collar 22 is preferably slit lengthwise. The unslit collar 22 (preferably the proximal end collar) is slipped over catheter 12 until sheath 18 is in place on balloon 10, then the slit collar 22 is opened, placed over the catheter and both collars are adhesively bonded to catheter. Preferably, sheath 18 is also bonded to all balloon lobes.

Where a single combination of rib 20 and collar 22 is used, as illustrated in FIG. 8, it is preferred that they be included at the proximal end of the balloon, to allow lower distal profile and lower required catheter retraction force. The distal end of sheath 18 should have the edge 24 configured to match the shape of the end lobe of spiral balloon 10 and be well bonded thereto.

Where a combination of rib 20 and collar 22 is used at one or both ends of sheath 18, the edges 24 of sheath 18 adjacent to rib 20 are shaped to have edges matching the shapes of lobes 16 at the ends of balloon 10. The edges are adhesively bonded to the end lobes to hold them securely in place and prevent "tenting" of the sheath into end channels and restricting blood flow, as occurs with prior circular sheath end configurations. Ribs 20 are circumferentially located so as to align with the end of lobe 16 so as to not obstruct the end channel 14 in any way.

In an alternate embodiment, a tubular preform is formed by conventional molding techniques, having a tubular center section conforming to sheath 18, two end extension tubes conforming to collars 22 and a conical transition section between sheath center portion 18 and collar portions 22. The conical transition sections are trimmed as discussed above to provide the desired shape for edges 24 as shown. Finally, one collar 22 is longitudinally slit so that the sheath can be slipped over the catheter and balloon with the slit end leading. The sheath is then bonded in place as described above.

While the sheath end configuration, ribs and collars may be cut from the basic tube shape in any suitable manner, laser cutting is strongly preferred. With laser cutting, we have found that a smooth edge is formed, with a small bead of material melted during cutting forming along the cut edge. This very tiny bead acts as a reinforced edge and eliminates any roughness or stress risers. Typically, the sheath preform tube is placed on a cylindrical mandrel so that the laser and/or mandrel can be moved as necessary to produce the desired cut pattern. Generally, the mandrel will be stepped where the sheath ends have a different diameter at the ends and will have a uniform diameter where the sheath diameter is to be uniform.

Any suitable programmable laser cutter (e.g., $CO_2$, YAG, eximer) may be used such as those used in stripping insulation from electrical conductors. A typical such machine is available from RTMC, Phoenix, Ariz. under the model WD-4 laser wire stripping machine designation. Typically, a $CO_2$ laser will be operated with a power output of from about 50 to 150 milliwatts. The rate at which cutting is performed depends on the power level setting and the type, color and thickness of material. Power level is typically set on the $CO_2$ laser by controlling the output pulse length and pulse repetition rated. If the cutting speed is too high for a selected laser pulse the cut will be a series of perforations rather than a continuous line. Thus, the power level and speed will be selected in accordance with the bead edge desired and the color, type and thickness of material, to provide the desired smooth, continuous cut. With the range of power and speed settings available, with various materials the cutting speed will vary from about 0.0001 to 1.0000 linear inches per second.

The completed assembly of catheter balloon 10 and sheath 18, partly cut away to show the interior, is provided in FIG. 5. As can be seen, The configuration of edges 24 of the sheath matches the end lobes 16 and is well supported when bonded thereto. This assures that the edge cannot fold inwardly to the point where the channels are obstructed and to assure full adhesion to the balloon.

Where sheath 18 is formed from compliant material, a retaining wire 26 is preferred, as shown in FIGS. 5, 6, 8 and 12. Where sheath 18 is formed from a non-compliant material, retaining wire 26 may be omitted, as illustrated in FIGS. 7 and 9. As seen in FIG. 5, when used, a retaining wire 26 has been wound along channel 14 and secured to the catheter with circumferential wraps at ends 28 to prevent expansion of the balloon channel area and keep those channels open for perfusion. Ribs 20 extend well down catheter 12 to collars 22 beyond wrapped ends 28 to positively secure sheath 18 in place.

Figure 10:
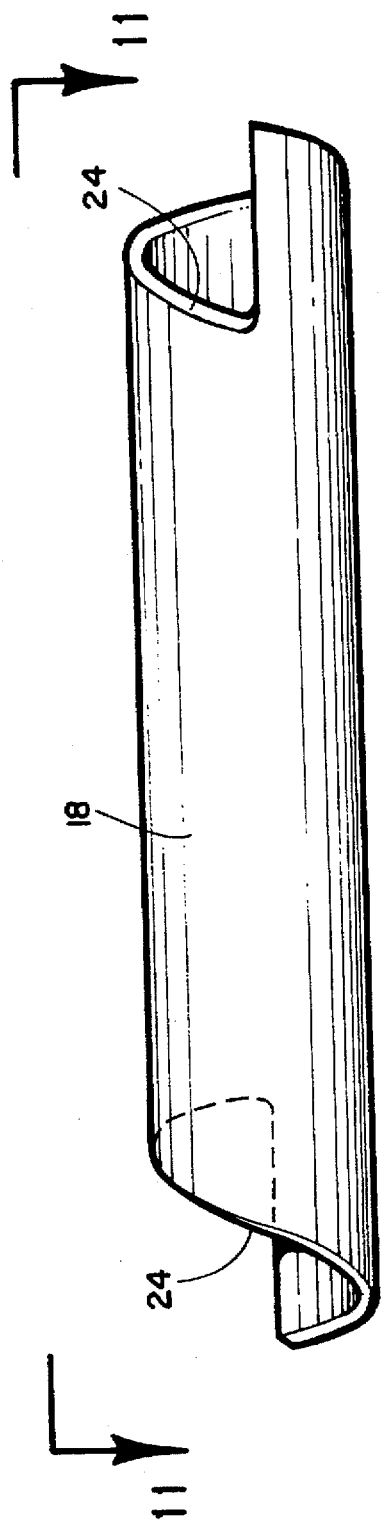
FIG. 10 is a side elevation view of the balloon sheath of FIG. 9 from the opposite side.
Figure 11:
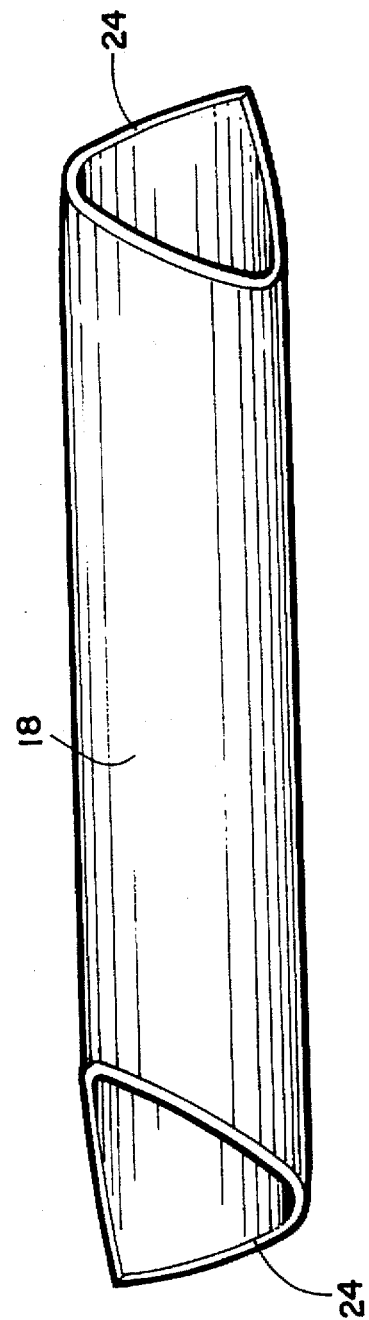
FIG. 11 is a plan view of the balloon sheath of FIG. 10.

FIGS. 9–11, where spiral balloon 10 is formed from a non-compliant (or semi-compliant) material and sheath 18 is well bonded to lobes 16, the combination of ribs 20 and collars 22 may be omitted. The ends of sheath 18 have beading along edges 24 detailed above and are configured in a spiral curve matching the shape of the end lobes 16, so there is no free edge to "tent" and cause an interference in flow through channels 14.

Examples of non-compliant or semi-compliant materials include polyethylene terephthalate (PET) or ethylene-vinyl acetate copolymer (EVA) or a combination of PET and EVA. Because different lesions appear to require different inflation pressures for dilatation, it is useful to have the ability to inflate over a wide range of pressures, typically 4 to 20 atm, while maintaining channel volume over that range. This enables balloon inflation to any pressure while still maintaining balloon diameter and balloon channel volume. A PET and EVA combination will permit this.

One rib 20 and collar 22 provides a safety advantage over no ribs 20 and collars 22. When only one rib 20 and collar 22 are used it is advantageous to place them at the proximal end of the balloon to not only lower the distal profile but also to lower the required guide catheter retraction force.

FIG. 12 shows an embodiment permitting perfusion of blood both through the main vessel in which the balloon and sheath assembly is positioned but also a side vessel extending from the main vessel at the balloon location. A plurality of openings 32 are formed in sheath 18 in alignment with channels 14 to allow blood to pass through to any side vessels. Openings 32 are preferably cut by the laser techniques described above to provide a reinforcing bead around each opening. Any suitable shape, number and arrangement of openings 32 may be provided. Openings may typically be round or short slots and may be regularly or randomly placed. While FIG. 12 illustrates openings 32 in conjunction with a sheath 18 of the sort illustrated in FIGS. 5 and 7, they may be used with any of the other embodiments, as desired, and may be used with an assembly with or without a retaining wire 26, as desired.

While certain specific relationships, materials and other parameters have been detailed in the above description of preferred embodiments, those can be varied, where suitable, with similar results. Other applications, variations and ramifications of the present invention will occur to those skilled in the art upon reading the present disclosure. Those are intended to be included within the scope of this invention as defined in the appended claims.

I claim:

1. A sheath for a catheter balloon of predetermined length and diameter and having a spiral axial pattern of lobes and channels which comprises:

a generally tubular body having a central axis and having an inside diameter and length sized to fit over said spiral catheter balloon;

ends of said tubular body at least partially configured to correspond to end lobes of said spiral axial lobe pattern;

wherein a plurality of openings are formed in said tubular body at locations corresponding to said spiral balloon channels when placed on said balloon; and wherein said ends of said tubular body have edges that include an integral bead.

2. A sheath for a catheter balloon of predetermined length and diameter and having a spiral axial pattern of lobes and channels which comprises:

a generally tubular body having a central axis and having an inside diameter and length sized to fit over said spiral catheter balloon;

ends of said tubular body at least partially configured to correspond to end lobes of said spiral axial lobe pattern; and the sheath further including a rib extending from at least one end of said tubular body generally parallel to said central axis and a collar secured to a distal end of said rib and sized to fit around said catheter adjacent to said balloon.

3. The sheath according to claim 2 wherein said tubular body has two open ends with a said rib and collar extending from each open end of said tubular body.

4. The sheath according to claim 3 wherein one said collar is tubular and has an inside diameter sized to slip over said catheter and one said collar is slit parallel to said axis for wrapping around said catheter.

5. A sheath for a spiral catheter balloon which comprises:

a generally tubular body having a central axis and having an inside diameter sized to fit over a spiral catheter balloon of predetermined outside diameter connected to a catheter;

said tubular body having at least one open end;

a rib extending from said open end of said tubular body generally parallel to said central axis; and a collar secured to a distal end of said rib and sized to wrap around said catheter adjacent to said balloon.

6. The sheath according to claim 5 wherein said tubular body has two open ends with a said rib and collar extending from each open end of said tubular body.

7. The sheath according to claim 6 wherein one said collar is tubular and has an inside diameter sized to slip over said catheter and one said collar is slit parallel to said axis for wrapping around said catheter.

8. The sheath according to claim 5 wherein said rib and collar are unitary with said tubular body, said body, said rib and said collar cut from a single elongated tubular preform.

9. The sheath according to claim 5 further including a plurality of holes through said tubular body, said holes arranged in a predetermined pattern corresponding to channels of said spiral balloon when said sheath is in place on said spiral balloon.

10. A balloon catheter assembly for use in medical procedures which comprises:

a catheter including a longitudinal lumen for delivery of a pressurized fluid therethrough;

a balloon on said catheter and sealed thereto for receiving said fluid and for inflation thereby;

said catheter extending entirely through said balloon;

said balloon having a spiral configuration comprising at least one outwardly extending spiral lobe separated by an inwardly extending channel;

said balloon channel secured to said catheter;

a generally tubular sheath overlying said balloon in stretched contact therewith when said balloon is inflated;

said tubular sheath bonded to said spiral lobe at predetermined locations;

said tubular sheath having ends, at least a portion of each end configured to correspond to said lobe at each end of said balloon and bonded thereto.

11. The balloon catheter assembly according to claim 10 wherein each end of said sheath includes an edge that is configured to correspond to said lobe at each end of said balloon and is bonded thereto.

12. The balloon catheter assembly according to claim 10 further including a narrow rib extending from at least one end of said tubular sheath, a collar means formed at a distal end of each said rib, said collar means wrapped around said catheter adjacent to said balloon and bonded to said catheter.

13. The balloon catheter assembly according to claim 12 wherein a said rib and collar is secured to each end of said sheath with each said collar bonded to said catheter adjacent to said balloon.

14. The balloon catheter assembly according to claim 13 wherein said rib and collar are unitary with said sheath, said sheath rib and collar being cut from a single elongated tubular preform.

15. The balloon catheter assembly according to claim 10 wherein a plurality of openings are formed through said sheath at locations corresponding to said balloon channel.

16. The balloon catheter assembly according to claim 10 wherein said sheath is bonded to said balloon by an adhesive applied between said lobe and sheath.

* * * * *